(12) United States Patent
Requejo

(10) Patent No.: US 6,352,210 B1
(45) Date of Patent: Mar. 5, 2002

(54) FRAGRANCED RICE HULL AIR FRESHENERS

(75) Inventor: Luz P. Requejo, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/553,783

(22) Filed: Apr. 21, 2000

(51) Int. Cl.⁷ .................................................. A24F 25/00
(52) U.S. Cl. ........................................... 239/34; 239/37
(58) Field of Search .............................. 239/34, 53, 56, 239/55, 57, 58; 502/411

(56) References Cited

U.S. PATENT DOCUMENTS

| | | | |
|---|---|---|---|
| 3,567,118 A | | 3/1971 | Shepherd et al. |
| 3,576,760 A | | 4/1971 | Gould et al. |
| 3,921,581 A | | 11/1975 | Brewer .......................... 119/1 |
| 4,283,011 A | * | 8/1981 | Spector ........................ 239/56 |
| 4,345,716 A | | 8/1982 | Armstrong et al. |
| 4,405,354 A | | 9/1983 | Thomas et al. |
| 4,587,129 A | | 5/1986 | Kliment |
| 4,619,911 A | * | 10/1986 | Goodwin et al. ........... 502/411 |
| 4,869,407 A | | 9/1989 | Booth, Jr. et al. |
| 4,906,488 A | | 3/1990 | Pera |
| 5,188,064 A | | 2/1993 | House |
| 5,679,334 A | | 10/1997 | Semoffet et al. |
| 5,904,028 A | | 5/1999 | Fujiura et al. |
| 5,976,503 A | | 11/1999 | Martin et al. |

FOREIGN PATENT DOCUMENTS

| | | |
|---|---|---|
| DE | 298 07 202 U1 | 4/1998 |
| EP | 0 965 541 A2 | 6/1999 |
| GB | 2313 060 A | 11/1997 |
| WO | WO 86/00496 | 1/1986 |

* cited by examiner

*Primary Examiner*—Lisa Ann Douglas

(57) ABSTRACT

Kits for consumer activated dispensers of active materials, such as air fresheners, are provided, comprising an inert carrier material, an active material, and a coloring agent. The inert carrier material is specifically designated as being rice hulls, a waste product of the milling of rice for consumption. The kit may take various forms, such as a container in which are packaged the appropriate amounts of rice hulls, fragrance, and colorant. In another form, the kit may comprise a sachet or pad containing the above materials. Further, a pad or sachet, containing rice hulls and a coloring agent if desired, may be subjected to the controlled continuous feed of a water solution of a fragrance, whereby a long term, consistent fragrancing is obtained.

18 Claims, No Drawings

FRAGRANCED RICE HULL AIR FRESHENERS

RELATED APPLICATIONS

Not applicable.

FEDERALLY SPONSORED RESEARCH OR DEVELOPMENT

Not applicable.

BACKGROUND OF THE INVENTION

1. Technical Field

The present invention relates to air fresheners comprising a fragrance and an inert carrier material, suitable for use in a sachet or a container such as a canister. In addition, the carrier material employed may be molded, or compressed, into a desired shape, which may be used as a carrier or fragrance source for a multitude of applications.

The carrier material used is a by-product of a major agricultural industry, and as such is both readily available and economical to use. Moreover, use of the carrier material as set forth herein constitutes an ecological solution for a disposal problem.

The air fresheners prepared in accordance with the present invention may take a variety of forms, determined by the specific materials provided, from compressed compositions, such as in the form of pads, sheets or bodies of compressed carrier material, which release fragrance by evaporation, to impregnated sachets containing particulate carrier and fragrance, which permit release of their contents only as a vapor. In addition, the fragranced carrier material may be placed in a canister or other suitable container, sealed to retain the fragrance, and subsequently opened, such as by removal of a barrier layer over openings in the container, to permit vapor release.

2. Background Art

It is known that gel materials, particularly hydrogels, may be prepared from a variety of differing polymeric resins. It is also known that such hydrogels may be impregnated with fragrance or deodorant materials. Many such gels have been sold to the public in the form of air fresheners, usually in glass or plastic containers for placement at a location of the consumer's choice. It is also known to provide various substrates as carriers for a fragrance material.

For example, Kliment, U.S. Pat. No. 4,587,129, teaches that lower alkyl alkenoate based hydrogels may be used for entrapping flavors and fragrances, for use as solid air fresheners or sachets.

Gould et al, in U.S. Pat. No. 3,576,760, disclose preparation of dry powders of water soluble hydroxyalkyl acrylate or methacrylate polymers useful as carriers for fragrances. Such materials as orange oil may be entrapped in the polymer for release upon contact with water.

In U.S. Pat. No. 3,567,118, Shepard et al describe dry products comprising fiber substrates impregnated with hydrophilic gels of (meth)acrylate polymers entrapping fragrance-emitting agents, which release fragrance when wetted.

Martin et al, in U.S. Pat. No. 5,976,503, and Booth, Jr., et al, in U.S. Pat. No. 4,869,407, teach air fresheners including means for active dispensing of fragrance. In Martin et al, the dispensing means employs heat, while Booth, Jr., et al employ a bellows to dispense fragrance from an impregnated paper based wafer disc.

Semoff et al, in U.S. Pat. No. 5,679,334, disclose a transparent gel air freshener containing an ornamental botanical.

Fujiura et al, U.S. Pat. No. 5,904,028, discloses a diffusing device containing a water-swellable gel carrying a fragrance agent. The device comprises a packet having a water permeable portion, and the patent teaches immersing the packet in water containing a fragrance whereby the resin absorbs the fragrance for subsequent release.

One problem with such air fresheners is that hydrogel materials or other resinous carrier materials are relatively expensive, and are outside the economic reach of many citizens of the poorer nations. What is needed, in many areas of the world, is an air freshener comprising relatively inexpensive materials, such that even those of limited means may be able to afford it.

SUMMARY OF THE INVENTION

The present invention is directed to a very low cost, convenient, consumer activated fragrance releasing device which retains its full fragrance capacity until activated, or opened to the atmosphere by the consumer. Moreover, this invention is directed to a means for utilization of a material which has up until now been considered a waste material, and a problem for disposal. Specifically, the invention comprises using, as an absorbent carrier material for air freshening fragrances or other active materials, the rice hulls resulting from the milling of rice. Such rice hulls are a large volume by-product of one of the largest agricultural crops world wide. Moreover, rice is a staple of both the diets and the economies of many third world nations, in which the average annual income of the populace is relatively low. Accordingly, the citizens of many of the countries which produce the largest volume of rice hulls are unable to readily afford such common home products as air fresheners, odor eliminators, fragrance dispensers, and insect repellents. It is a purpose of the present invention to not only eliminate a waste product for which there has been little prior use, but to provide a device for the dispersal of active materials which is more highly affordable.

Thus, the invention is directed to an actives dispensing device comprising a very inexpensive, natural carrier material, coated or impregnated with a suitable fragrance, air freshener, or other active material so as to provide a most economical source thereof for the consumer. Applicant has found that the use of rice hulls, obtained as a by-product of the milling of rice, provides a very absorbent carrier material, which is capable of retaining a high volume of a chosen liquid fragrance, etc, for later vaporization or release to the atmosphere.

In its broadest sense, the invention comprises providing to the consumer a package of a dry particulate material carrying a fragrancing material, and a colorant if desired, in an appropriate container. In another embodiment of the invention, dry rice hulls, impregnated with colorant, may be mixed with a separately provided solid or liquid fragrance, followed by drying, if necessary, to an appropriately low liquid level. The presence of water in the rice hulls is undesirable, due to decomposition thereof and possible fermentation. The coloring agent, may of course, be present in the fragrance, rather than in the rice hulls, if so desired. Upon stirring or shaking of the carrier and the fragrance and coloring agent, a colored mixture is formed, having the fragrance absorbed therein for release by evaporation over a period of time.

In another embodiment of the invention, a sachet is prepared, comprising a vapor permeable package of such material as shall permit the passage of vapors, such as fragrances, from the interior of the package, but shall not permit liquid to flow inwardly. Such materials are known for use in personal care products, and permit the passage of liquid in one direction only. This type of material may comprise conically apertured polyethylene film, having small diameter openings designed to permit flow of liquid in one direction, but to close and prohibit back flow of the liquid. Such materials shall henceforth be referred to herein as having one way permeability to water. Vapors are able to escape from the microscopic openings in the surface of such materials, however, so that if a fragrance is enclosed within the material, the evaporation of such fragrance may occur as desired. While it is desirable that the entire sachet be of the same material, it is possible for only a limited amount of the surface area of the sachet be so characterized, provided that the remaining surface area be impermeable to water. In the sachet may be combined dry rice hulls, a colorant if desired, and a fragrance material, which may be particulate or a liquid. While it is preferred that the liquid be fully absorbed by the rice hulls, use of a sachet material having one way or no permeability to liquid enables one to provide a larger volume of liquid active material.

While the present disclosure speaks in terms of fragrances and fragrancing materials, it is to be understood that this invention is intended to be inclusive of all types of active materials suitable for release as a vapor, from either a solid or liquid form, at temperatures normally encountered in ambient conditions, or at slightly elevated temperatures such as may be achieved by use of a candle, electrical heating means, or other heating means capable of elevating the temperature to a point at which vaporization of an active material may be achieved. The term active material is to be understood to include various materials selected from the group consisting of fragrances, air fresheners, deodorizers, odor eliminators, malodor counteractants, insecticides, insect repellants, medicinal substances, medicaments, disinfectants, sanitizers, mood enhancers, aroma therapy compositions, and mixtures thereof. Most commonly, such materials may be selected from the group consisting of air fresheners, fragrances, deodorants, disinfectants, and insecticide active agents, and may be provided as solids, liquids, or gels.

In still another related embodiment of the invention, a pad of compacted active material impregnated or coated rice hull material is placed in a convenient location, such as a dish or bowl, and allowed to release the active material, such as an air freshening fragrance, to the atmosphere. By the term pad, applicant refers to a shaped body, such as a substrate or structure of uniform nature, as opposed to a sachet, which comprises an outer cover surrounding separate and particulate contents. Such a pad may constitute a compressed block of rice hulls, or a sheet like material, such as a non-woven fabric, e.g. felt, as well as paper, or cardboard. While rice hulls are cellulosic, there may also be employed other fibers such as nylon, acrylonitrile fibers, polyvinyl chloride fibers, wool, and polyethylene terephthalate fibers to aid in the binding or shaping of the pad. A preferred form comprises a paper or cardboard like structure, referred to as a sheet material.

In such an embodiment, the fragrance may be in a solid form, mixed with the rice hulls in the pad, or alternatively, may be added in liquid form to the pad or sheet forming the structure, absorbed thereby, and evaporated therefrom. In still a further alternative to this embodiment, the shaped body of rice hulls may be coated or impregnated with a liquid fragrance, either in manufacture, or by the consumer.

In such an instance, applicant envisions providing a source of fragrance in addition to a rice hull substrate or sachet, to which the fragrance is added by the consumer to "activate" the dispenser. After evaporation of the fragrance, additional fragrance may be added to the rice hulls, which are not consumed or effected by the fragrancing material, to "recharge" or "refresh" the air freshener. At such a time, the consumer would have the option of using either the same fragrance, or changing fragrance to an alternative scent if so desired. It is also possible for the consumer to use the inert rice hull carrier body to provide a substrate for the distribution of such materials as insecticides, insect repellents, aroma therapy materials, medicaments, etc., at the consumer's option.

Aside from being provided as a sachet, or as an impregnated substrate of molded or compressed materials, the rice hull carriers employed in the present invention may be provided as loose hulls or agglomerations thereof in a canister or container having vent holes for circulation of air from the exterior to the interior and vice versa, so as to permit flow of a fragrance or other volatile active material included in the rice hull carriers. Thus, one may prepare a canister of rice hulls, saturated with a fragrance material, said canister having ventilation holes therein, said holes being covered or closed by a lid, or by a peelable layer of a vapor impermeable material, so as to prevent loss of the fragrance until such time as it is desired to open or activate the dispenser by peeling away the vapor impermeable material, or lifting away the tight fitting lid. The consumer may thus expose the ventilation openings or holes, which are of a size so as to restrict the rice hulls from escaping from the container, but large enough to permit vaporization of the fragrance material. In such an embodiment, the material to be dispensed may be any active material such as previously discussed, including not only fragrances, but insect repellents, sanitizers, mood enhancers, etc.

DETAILED DESCRIPTION OF THE INVENTION

In the simplest embodiment of the invention, the consumer is provided a sachet form of an air freshener device. The basic components thereof comprise a measured amount of a dry rice hull substrate material which is an inert carrier for the desired active material, such as a fragrance. Rice hulls, as a basic by-product of the preparation of rice for food, provide a carrier which is quite advantageous, for reasons of stability, low cost, high liquid absorbency, and ease of use. The rice hulls are preferably provided as a solid particulate, packaged in a bag, for example, such as a sachet, characterized as having permeability to vapor. A chosen active material may be included with the rice hulls, such as by saturating the dry hulls therewith, or by including a solid fragrance bearing material or solid active ingredient per se with the rice hulls, or by spraying the sachet with a selected active material, such as a fragrance oil.

It is desirable that such a sachet packet be enclosed in an air-tight enclosure, bag, or container, for distribution and sale to the consumer, so as to limit the undesirable access thereto of water, humidity or air borne moisture, as well as to limit the premature release to the atmosphere of the fragrance or other active material included therein. Further, such packaging should preferably be easily openable, economically produced, and ecologically safe for disposal.

As indicated, packaged with the rice hulls in the dispenser or sachet may be a fragrance material, such as a conventional air freshener fragrance, in liquid form, either as a water soluble solution, or as a solvent based solution, or in solid form, such as a freeze dried or encapsulated powder. The fragrance material may absorbed by the rice hulls, or if in solid form, mixed therewith. Exemplary of such fragrance materials are such fragrance ingredients which may be used to create satisfactory aromas, including but not limited to myrrh, cedarwood, cedrenol, cedrol, birch, methyl salicylate, fir balsam, sandalwood, santalol, juniper, benzoin, coniferyl benzoate, thyme, thymol, bay, eugenol, myrcene, basil, camphor, methyl cinnamate, cinnamon, cinnamic aldehyde, rosemary, clove, and borneol.

Preferably, the fragrance or air freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance may be a synthetically formed material, or a naturally derived oil such as oil of bergamot, bitter orange, lemon, mandarin, caraway, geranium, lavender, orange, origanum, petitgrain, white cedar, patchouli, lavandin, neroli, rose absolute, and the like.

In addition, a wide variety of chemicals are known for perfumery, such as aldehydes, ketones, esters, alcohols, terpenes, and the like. A fragrance can be relatively simple in composition, or can be a complex mixture of natural and synthetic chemical components. Synthetic types of fragrance compositions may be employed, either alone or in combination with natural oils, as described in U.S. Pat. Nos. 4,324,915; 4,411,829; and 4,434,306. Other artificial liquid fragrances include geraniol, geranyl acetate, isoeugenol, linalool, linalyl acetate, phenethyl alcohol, methyl ethyl ketone, methylionone, isobomyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. Such gels may be used to apply the fragrance to the rice hull. A fragrance ingredient can also be in the form of a crystalline solid, which has the ability to sublime into the vapor phase at ambient temperatures. A crystalline fragrance material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability for use in the present invention. Among the preferred fragrances are such fragrance materials as lilac, jasmine, and rose, citrus odors such as lemon, orange, or lime, and apple type fragrances such as green, red, and golden delicious.

The invention may also constitute a kit which comprises a suitable container for the rice hull carrier, and a breakable vial or container of active material, and may contain instructions for the consumer to activate the dispenser by breaking the vial or container so as to release the contents to be absorbed by the rice hulls. In such an embodiment, a sachet type of air freshener may be provided, in which the rice hulls are contained within a vapor permeable (and preferably decorative) outer fabric, and the fragrance, in either a liquid form or gel, is contained within a glass or breakable plastic container, such as a vial, which is contained within an inner woven pad, of a type known in the art to which the present invention pertains, which prevents the glass or plastic, when broken, from contacting the outer fabric. To activate the air freshener device of this embodiment, the consumer merely breaks the glass or plastic vial, without removing it from the fabric sachet, by flexing (or by otherwise causing the vial to open), thereby releasing its contents, said contents comprising the fragrance or active material of choice. The fragrance or active material, once released from the vial, is then absorbed by the woven pad, and thence by the rice hulls with which the woven pad is in contact. As indicated, the woven pad serves to contain the broken parts of the vial, protecting both the consumer and the outer fabric of the sachet from being injured.

Of course, other variations of this embodiment are readily apparent. For example, one may provide a kit comprising a fragrance vial, packaged separately from the rice hull carrier, which may be provided, for example as a molded or shaped body, or as a small container of loose hulls. If provided thusly, the consumer could place the hulls in a suitable container for the preparation of the dispenser. The container could be a dish, bowl, jar, or such, of suitable volume and aesthetically pleasing, made of an inactive material, such as glass or plastic which will not react with any of the components of the kit, or with any solvent material present in the fragrance. Glass or hard transparent plastic is preferred. The consumer could then open the fragrance vial, such as by breaking, or preferably by opening a closure such as a lid or screw-on cap, and distribute the fragrance material over the rice hulls, and mix to assure that the fragrance is absorbed therein.

In a preferred embodiment, the kit comprises a glass jar, such as commonly used for jar candles, containing a small plastic bag of rice hulls, and a small glass or plastic vial of fragrance. The kit may further comprise a plastic lid, having small openings therein, whereby fragrance may be released to the atmosphere after the air freshener kit has been activated by the addition of the fragrance to the rice hulls by the consumer, and reclosure with the lid, which also serves to prevent accidental exposure of the contents such as by children touching or playing with the contents. The lid may also be designed to enhance air flow for better fragrance delivery to the environment.

When the consumer wishes to avail himself or herself of the air freshener device, the consumer may open the component packages, and mix the contents thereof in the container provided, or in a suitable container of the consumers choice. Thus, the consumer may mix the rice hulls, a colorant if present, and the fragrance material. After addition of the fragrance or other active material to the rice hulls, the consumer may stir, mix, or shake the mixture to assure full contact of all of the components present. The fully mixed components may then be put aside for a few minutes, for the complete absorption of the fragrance or other active material by the rice hulls. The container may then be left in a desired location for evaporation of the active material to the atmosphere. Such kits may readily be provided with a variety of active materials, or the components may be sold as separate units, enabling the consumer to re-use a rice hull carrier package or absorbent pad or block for a variety of differing active materials. For example, the consumer might select a mood enhancing fragrance for a specific area of the home, or an air freshener or odor counteractant for the kitchen or bathroom.

As an example of the above embodiment of the invention, a rice hull air freshener kit is prepared, comprising a small plastic container containing from about 0.5 to about 2 grams of clean, dry rice hulls, and a small vial containing from about 2 to about 8 grams of a liquid jasmine fragrance. The rice hulls are premixed with about 0.04 weight percent of a coloring agent, such as Red F-5B, from Clairiant. The rice hulls and the fragrance are provided in a small candle jar, having a plastic lid. Upon opening of the lid and removal of the contents, the rice hulls and fragrance are mixed in the candle jar, forming a light red mixture containing the fragrance. The fragranced rice hulls are left open to the atmosphere, with no cover, providing an air freshening effect. The finished air freshener may be contained in a variety of containers. The greater the surface area of the rice hulls exposed to the air, the stronger the fragrance strength, due to the greater number of fragrance molecules released into the atmosphere. Smaller mouth containers, on the other hand, will have a weaker fragrance strength, due to a lower evaporation rate, but a longer product life.

In another embodiment of the invention, a kit is provided to the consumer as set forth above, wherein the rice hull carrier is provided in the form of a sachet, characterized by having permeability to vapors, wherein the fragrance material is included within the sachet. For example, the fragrance may be provided as a solid particulate material, either crystalline or powder, or as a spray dried fragrance, either mixed with or upon the surface of the rice hulls. Suitable forms of solid active materials include spray dried powders, and encapsulated fragrances. Alternatively, the active material may be a liquid, included in a breakable container within the sachet, which the consumer may squeeze or flex to break open and release the contents thereof. Upon release of the liquid active material to the sachet, the liquid is rapidly absorbed by the rice hulls, which are constrained by the packet.

In another form of the invention, a substrate, such as a pad, sheet, or block of molded or felted rice hulls, may be coated or impregnated with a mixture of fragrance or other active, dried, and provided to the consumer in moisture resistant packaging which does not permit the vaporization of the fragrance or active material. Such a substrate pad need not be limited to sheet materials, but may include pressed bodies of rice hull cellulosic material, which may include small figurines or decorative shapes such as pine trees, flowers, animals, rings, coasters, etc. This substrate may then be removed from the moisture resistant packaging, to provide an air freshener which will release fragrance over a period of time when placed in a location of the consumer's choice for extended air freshening.

As an example of this embodiment of the invention, a cellulosic pad comprising crushed rice hulls, is impregnated with a spray dried lemon oil fragrance, in a non-aqueous carrier, dried, and set aside. After drying, the impregnated pad is hung from a convenient location, and provides air freshening for a number of days.

In still another form of the invention, a pad of rice hulls is prepared, containing no fragrance, and dried. The pad is then placed in a small bowl, open to a controlled flow of a fragrance oil, or water containing a water-soluble fragrance. Alternatively, the bowl may be attached to a reservoir of fragrance solution having a controlled rate of release of solution equivalent to the evaporation rate of the liquid absorbed into the pad. This form of air freshener has a life span determined by the volume of water and/or fragrance available. Since the rice hull pad acts merely as an inert surface for the evaporation of fragrance oil or fragrance contained in water, which can be provided separately, for example, this pad provides a source of consistent fragrancing which is capable of being stored for an extended period of time, and economically shipped. Further, since the fragrance being emitted to the atmosphere is replenished by the addition of fresh fragrance, at the rate of fragrance evaporation, this form of air freshener provides consistent and fresh fragrancing for as long a period as a source of a liquid fragrance is available. Hence, the consumer could purchase separate, and perhaps differing, containers of fragrance, and continue to obtain an air freshening effect indefinitely, by merely replacing the container of fragrance as it is emptied.

These rice hull pads were found to constitute very economical forms of air freshener substrates, whether the fragrance was present in the pad, or in a liquid with which the pad was subsequently contacted by the consumer. Due to the fact that there was no liquid present in the pad, shipping costs are minimized. This form of packaging also permits great flexibility in terms of the product offered the consumer. By packaging the pad with a container for controlled contact with the chosen active material, i.e. a metering bottle and tray to hold the pad and into which the desired liquid active may be metered, the consumer may receive an economical, totally dry system which may be opened, easily assembled, and activated by addition of a chosen solution, packaged separately, to the metering bottle.

Alternatively, rice hull pads may be sold separately, having various fragrances therein, so as to offer the consumer replacement pads of varying fragrance. Or, various solutions of differing fragrance may be offered to be utilized with rice hull pads or blocks (having no fragrance), so as to permit the consumer the opportunity to vary the fragrance as desired.

INDUSTRIAL APPLICABILITY

While the present invention has been described with respect to what is at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

I claim:

1. A kit for the preparation of a dispenser of active materials, said kit comprising a measured quantity of dry rice hulls, a measured quantity of an active material selected from the group consisting of fragrances, air fresheners, deodorizers, odor eliminators, malodor counteractants, insecticides, insect repellants, medicinal substances, medicaments, disinfectants, sanitizers, mood enhancers, aroma therapy compositions, and mixtures thereof, and a container in which said measured quantities of rice hulls and active material may be mixed.

2. The kit of claim 1, wherein said container in which said measured quantities of rice hulls and active material may be mixed is a sachet.

3. The kit of claim 2, wherein said rice hulls and active material are packaged separately.

4. The kit of claim 3, further comprising a coloring agent.

5. The kit of claim 4, wherein said active material is selected from the group consisting of air fresheners, fragrances, deodorants, disinfectants, and insecticide active agents.

6. The kit of claim 5, wherein said active material is a liquid fragrance enclosed within a breakable container.

7. The kit of claim 5, wherein said active material is a solid.

8. A dispenser of an active material, comprising a container, an active material, and an inert carrier for said active material, said carrier comprising rice hulls, wherein said active material is provided in a separate container to be added to said inert carrier so as to activate said dispenser.

9. A dispenser as set forth in claim 8, wherein said active material is selected from the group consisting of fragrances, air fresheners, deodorizers, odor eliminators, malodor counteractants, insecticides, insect repellants, medicinal substances, medicaments, disinfectants, sanitizers, mood enhancers, aroma therapy compositions, and mixtures thereof.

10. The dispenser of claim 8, wherein said rice hull carrier is present in the form of a pad.

11. The dispenser of claim 8, wherein said active material is present as a solid material.

12. The dispenser of claim 9, wherein said active material is provided as a liquid which is absorbed by said rice hull carrier.

13. The dispenser of claim 8, wherein said container comprises a sachet.

14. The dispenser of claim 8, wherein said container has openings therein for the release of vapors of said active material, said openings having removable coverings for selected release of said vapors.

15. A dispenser of an active material, selected from the group consisting of fragrances, air fresheners, deodorizers, odor eliminators, malodor counteractants, insecticides, insect repellants, medicinal substances, medicaments, disinfectants, sanitizers, mood enhancers, aroma therapy compositions, and mixtures thereof, said dispenser comprising a container holding an inert carrier for said active material, said carrier comprising rice hulls, said container configured so as to expose said inert carrier to the atmosphere so as to permit vaporization of said active material from said carrier, wherein said active material is provided in a separate container to be added to said inert carrier so as to activate said dispenser.

16. The dispenser of claim 15, wherein said active material is provided in a container which is broken so as to release said active material to be absorbed by said inert carrier.

17. The dispenser of claim 15, wherein said active material is provided as a liquid which is permitted to drip upon said carrier material at a rate of flow selected so as to provide a constant rate of evaporation of said active material.

18. The dispenser of claim 17, wherein said carrier material comprises a pad.

* * * * *